(12) United States Patent
Taylor

(10) Patent No.: US 8,248,231 B2
(45) Date of Patent: Aug. 21, 2012

(54) MONITORING SYSTEM

(75) Inventor: Peter James Taylor, Mount Waverley (AU)

(73) Assignees: Sensor Technology and Devices Ltd. (GB); Peter James Taylor, Victoria (AU)

( * ) Notice: Subject to any disclaimer, the term of this patent is extended or adjusted under 35 U.S.C. 154(b) by 1361 days.

(21) Appl. No.: 10/495,349

(22) PCT Filed: Nov. 8, 2002

(86) PCT No.: PCT/AU02/01530
§ 371 (c)(1),
(2), (4) Date: May 7, 2004

(87) PCT Pub. No.: WO03/039361
PCT Pub. Date: May 15, 2003

(65) Prior Publication Data
US 2004/0252031 A1    Dec. 16, 2004

(30) Foreign Application Priority Data
Nov. 8, 2001 (AU) .............................. 8751

(51) Int. Cl.
*G08B 1/08* (2006.01)
(52) U.S. Cl. ........... 340/539.12; 340/539.11; 340/573.1; 128/903; 128/904; 600/301
(58) Field of Classification Search .............. 340/539.1, 340/539.12, 573.1, 573.4, 539.11; 600/300, 600/301, 484–490; 128/900–925, 696
See application file for complete search history.

(56) References Cited

U.S. PATENT DOCUMENTS

| | | | | |
|---|---|---|---|---|
| 4,827,943 A * | 5/1989 | Bornn et al. | ................. | 600/481 |
| 5,417,222 A * | 5/1995 | Dempsey et al. | ............. | 600/509 |
| 5,873,369 A * | 2/1999 | Laniado et al. | ............... | 600/300 |
| 5,907,291 A * | 5/1999 | Chen et al. | ............... | 340/870.16 |
| 6,057,758 A * | 5/2000 | Dempsey et al. | ........ | 340/539.12 |
| 6,093,146 A * | 7/2000 | Filangeri | ....................... | 600/300 |
| 6,327,495 B1 * | 12/2001 | Iwabuchi et al. | ............. | 600/547 |
| 6,366,871 B1 * | 4/2002 | Geva | ............................ | 702/188 |
| 6,416,471 B1 * | 7/2002 | Kumar et al. | ................. | 600/300 |
| 6,428,475 B1 * | 8/2002 | Shen | ............................. | 600/300 |
| 6,485,416 B1 * | 11/2002 | Platt et al. | ..................... | 600/300 |
| 6,485,418 B2 * | 11/2002 | Yasushi et al. | ................ | 600/300 |
| 6,540,663 B1 * | 4/2003 | Vau et al. | ........................ | 600/27 |
| 6,544,171 B2 * | 4/2003 | Beetz et al. | ................... | 600/300 |
| 6,558,321 B1 * | 5/2003 | Burd et al. | ..................... | 600/300 |
| 6,607,484 B2 * | 8/2003 | Suzuki et al. | ................. | 600/300 |
| 6,664,893 B1 * | 12/2003 | Eveland et al. | .......... | 340/539.12 |
| 6,749,566 B2 * | 6/2004 | Russ | ............................. | 600/300 |
| 6,903,657 B2 * | 6/2005 | Kwoen | ...................... | 340/573.1 |
| 7,181,505 B2 * | 2/2007 | Haller et al. | .................. | 709/219 |
| 7,542,878 B2 * | 6/2009 | Nanikashvili | ................ | 702/188 |
| 2004/0059205 A1 * | 3/2004 | Carlson et al. | ............... | 600/310 |
| 2006/0089786 A1 * | 4/2006 | Soehren | ....................... | 701/200 |
| 2007/0174515 A1 * | 7/2007 | Sinclair et al. | ................. | 710/62 |

* cited by examiner

*Primary Examiner* — Hung T. Nguyen
(74) *Attorney, Agent, or Firm* — Drinker, Biddle & Reath LLP

(57) ABSTRACT

A monitoring system having a device on a person which can process and transmit signals from at least one biosensor and a receiver located close to the patient, which can receive these signals. The receiver, which may be a portable telephone, can process the signals and provide an indication of the parameter(s) being monitored and may also, or as an alternative, forward the received signals to a remote monitor. The monitoring system may further include a device for indicating when the transmitter is not receiving a signal from the transmitter and can also include a device so that when a parameter reaches a critical care level, a warning signal is given. The monitoring system is such that the person being monitored is effectively not limited to remaining within a required distance of a fixed part of the system.

16 Claims, 1 Drawing Sheet

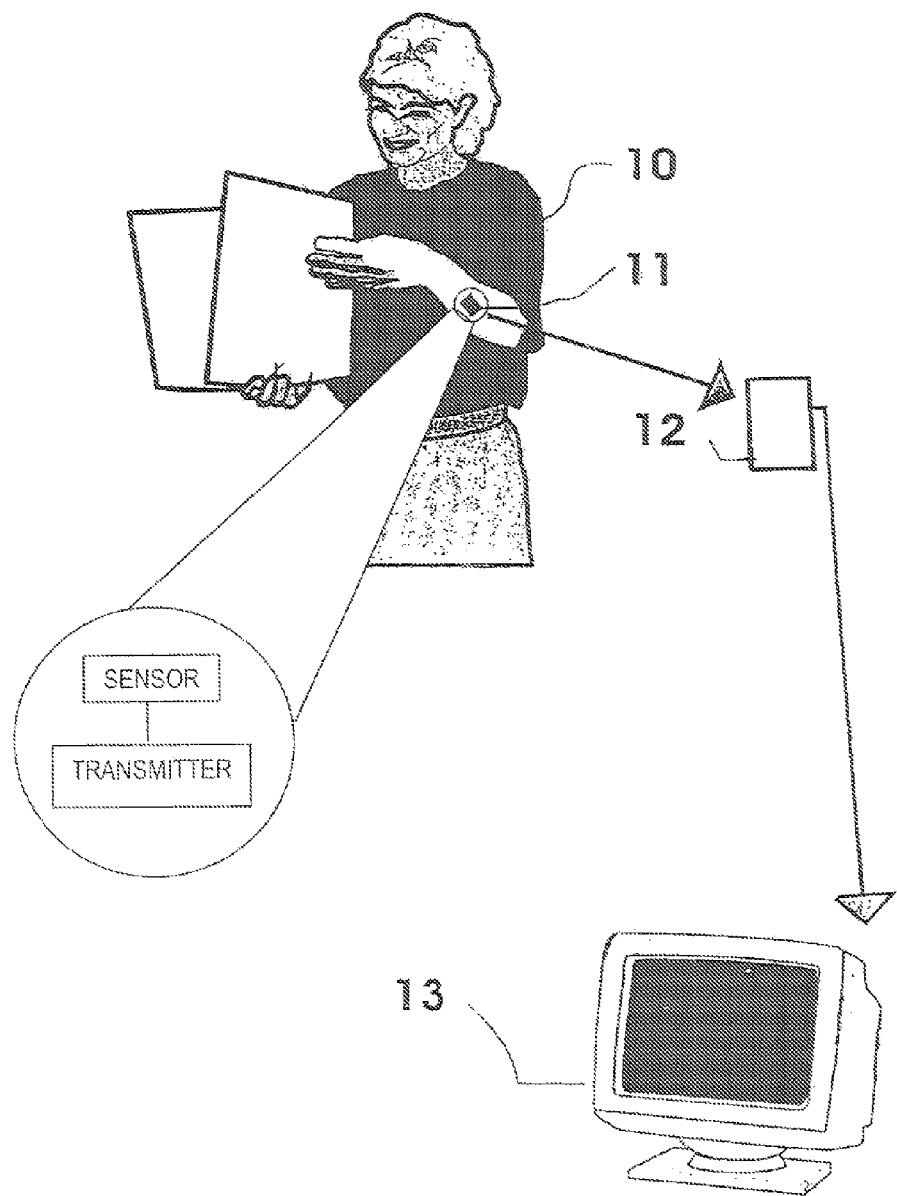

MONITORING SYSTEM

BACKGROUND OF THE INVENTION

1. Field of the Invention

This invention relates to a monitoring system and specifically to a system for use in medical applications.

2. Description of the Prior Art

There are particular areas where relatively constant monitoring of certain vital signs of a person are desirable but, at the same time the person is ambulatory and does not need hospitalisation.

For example, for a person who has a heart attack occurrence it may be desirable to monitor heart rate over a relatively short period whilst the person is recuperating whilst an elderly person with a heart condition or, say, diabetes may need constant monitoring for substantial periods, such as years.

There are, today, many sophisticated monitoring systems one, for example, is described in Patent Cooperation Treaty Application No. PCT/AU01/01240 where various types of monitors can be connected to an electrode and, provided the monitor is close to the electrode, then it receives a message from the electrode so the user does not have to be physically connected to the monitor.

It is also known to use the telephone system to provide a monitor with input material, such arrangements being commonly used with ECG's where the result of the electrodes are transmitted by way of a modem on a standard telephone line to remote recording apparatus. There are also similar systems, for example as illustrated in PCT Patent specification WO 94/01039 of Jacob Segalowitz where the transmission is by way of a radio transmitter. These systems are basically short term arrangements whilst a particular reading is being taken.

There has also been proposed, in U.S. Pat. No. 6,416,471 and arrangement where vital signs are measured and are fed to a small signal transfer unit which transmits signals to a base station which, in turn can transmit signals along conventional telephone lines. It is necessary for tis system to work that the signal transfer unit remain within a limited distance of the base station.

SUMMARY OF THE INVENTION

It is to monitors of this general type that this invention relates and, specifically, to a system where the person is generally not restricted to being within a specific distance from a base station.

It is also an aspect of the invention that the vital signs can be provided at a remote monitor but which can be provided with a local indication of various parameters.

The invention, in its broadest sense, includes a monitoring system having a means on a person which can process and transmit signals from at least one biosensor and a receiver located close to the patient, which can receive these signals.

It is preferred that the monitoring system can forward the received signals to a remote monitor.

It is also preferred that the receiver has a display and includes means whereby the received signals can be again processed to provide on the display the reading of the biosensor.

It is also preferred that the receiver is a mobile phone, preferably a cellular phone.

In a particular form of the invention the cellular phone incorporates the receiver and chipset which performs a primary analysis according to pre-set and adjustable values, and a monitor which can provide, on the phone screen, an indication of the parameter being maintained and the current value.

Also the phone may be arranged so that when the parameter reaches a pre-determined value, the phone automatically dials a more sophisticated monitor for the parameter which reads the value and transmits details to a remote monitoring facility where human intervention may occur.

The phone may also have an arrangement whereby if any parameter being monitored reaches a critical level there is a warning alarm to the user or his/her carer and physical resources marshalled to deal with the event.

The system may also have an arrangement whereby if the separation between the phone and the transducer is greater than the transmitters range of 1-2 metres then the phone will effect a warning signal.

BRIEF DESCRIPTION OF THE DRAWING FIGURE

In order that the invention may be more readily understood we shall describe one particular arrangement of the invention in relation to the drawing.

DETAILED DESCRIPTION OF THE DRAWING FIGURE AND PREFERRED EMBODIMENTS OF THE INVENTION

Basically there are two components.

The first is the electrode system 11 which is worn by a person and which provides an is indication of the parameter or parameters being monitored. In the drawing this is shown on the arm of the user 10 but depending on the parameters, this may be on other parts of the body. The second is the cellular phone 12 which can receive this information.

In a practical arrangement, there can be considered to be a third component which is the remote monitoring facility 13.

As far as the electrode arrangement is concerned, it could be considered to be similar to that in the Patent Cooperation Treaty application previously mentioned but may take any form.

Basically, there must be at least one biosensor which gathers data relating to the parameter being measured which could, for example, be heart rate and rhythm, blood pressure, temperature, respiration, as well as Oxygen, Carbon dioxide and pH levels in the blood or any of a number of other different biochemical or physiological parameters.

There will, of course, be any necessary circuitry to, say, digitise the results of the biosensor(s), if these are originally in analogue form.

The transmitter transmits its signal to a receiver inbuilt or attached to the cellular phone 12 which is adapted to be relatively close to the transmitter and which may be arranged to provide an aural or visual warning if it is further away than a maximum distance.

In one form, this warning may simply be a signal from the phone itself or it could be that the phone is caused to operate to dial an external number to provide an indication that the spacing is unsatisfactory.

The phone is provided with circuitry to receive the signal from the transmitter and to convert it back to an indication of the parameter being measured.

This parameter can be displayed on the phone screen either as instantaneous FIGURES, a series of figures on a time basis or a plot on a time basis of the value of the parameter.

This means that the patient or a physically located carer have means whereby they can ascertain the status of the parameter.

The telephone also has means whereby the information can be transmitted to the remote monitor 13, directly or via the internet, either on a regular basis in which case the phone may have a memory and a hierarchy or calls depending on the event and the severity. The phone can store particular values of the parameter or it may simply forward the present value and also have means whereby, on the parameter reaching a pre-determined warning condition the phone automatically dials the remote monitor, forwards the information to it and possibly actuates an alarm at the remote monitor.

The invention can also be used in association with GPRS (General Packet Radio Service) in which there is effectively a permanent connection and a cost per kilobyte of data and under such a system, should an alarm state be reached, a packet of digitised information is automatically sent to the remote monitor without the necessity of actually dialling the monitor.

Thus, the person in ultimate charge of monitoring the condition of the patient will be rapidly made aware of any change in the parameter which could be a change for the worse.

This person may then take steps to initiate a treatment program for the patient which, in itself, could be initiated through the phone automatically initiating the operation of, say, a bolus of medication into a drip. More usually, the person will contact the patient or the carer and notify them of the necessity of action being taken.

It can be that several different parameters are monitored on the same patient and they can selectively be displayed on the mobile phone screen on operation of specific keys and these may each have a different telephone number to be dialled out on a pre-determined change in the parameter so that different properties, even in different areas, can be notified when particular parameters vary.

It will be seen in that the invention provides a means whereby ambulatory patients who could well normally need hospitalisation can be maintained at home or in a non-hospital environment whilst having their vital signs monitored as effectively as would be the case if they were hospitalised, and with good warning if there is any change in their state. At the same time, where the receiver is a cellular phone, the person is restricted only by the area of coverage of the cellular system when means that for most people, particularly those in urban areas, that they are effecively non-restricted as far as movement is concerned.

Furthermore, those patients with manageable health conditions can be closely monitored without undue imposition or intrusiveness.

Whilst we have described one particular method of using the invention it will be appreciated that the invention could also be applied to hard wired telephone systems or even radio systems should this be required. It will also be understood that the types of electrodes and transmitters used could be varied to suit particular circumstances and it could also be that the degree of manipulation of the incoming signals by the telephone system can be modified depending upon particular requirements and uses.

The transmission from the transmitter to the telephone 12 can be in any required way, such as using Bluetooth technology or Ultra Wide Band (UWB) technology.

I claim:

1. A monitoring system, comprising:
   at least one biosensor for generating a biometric signal from a measured parameter of a person;
   a transmitter connected to the biosensor for transmitting the biometric signal using Bluetooth technology; and
   a receiver not disposed in or coupled to a mobile telephone, for receiving the transmitted signal, displaying the biometric signal on a display device of the receiver, and wirelessly forwarding the signal to a remote monitor using General Packet Radio Service (GPRS).

2. The monitoring system of claim 1, wherein the display provides an indication of the parameter being measured, and the signal is displayed as an instantaneous FIGURE, a series of figures on a time basis, or a plot on a time basis of the parameter value.

3. The monitoring system of claim 1, wherein the measured parameter is the person's heart rate, heart rhythm, blood pressure, temperature, respiration, blood oxygen level, blood carbon dioxide level, or blood pH level.

4. The monitoring system of claim 1, wherein the received signal is automatically forwarded to the remote monitor when the measured parameter exhibits a predetermined property.

5. The monitoring claim 1, wherein the received signal is periodically or selectively forwarded to the remote monitor.

6. The monitoring system of claim 1, wherein the received signal is continuously forwarded to the remote monitor.

7. The monitoring system of claim 1, wherein the receiver establishes a warning condition if it is not receiving the biometric signal.

8. The monitoring system of claim 1, wherein the receiver establishes a warning condition if the biometric signal exhibits a predetermined property.

9. The monitoring system of claim 8, wherein predetermined property is crossing a predetermined threshold.

10. The monitoring system of claim 8, wherein the predetermined property is related to a predetermined waveform.

11. The monitoring system of claim 8, wherein the warning condition automatically initiates an alarm at the receiver.

12. The monitoring system of claim 11, wherein the alarm is an audio or visual signal.

13. The monitoring system of claim 8, wherein the warning condition automatically initiates an audio or visual alarm at the remote monitor.

14. The monitoring system of claim 8, wherein the warning condition selectively initiates an audio or visual alarm at the remote monitor.

15. The monitoring system of claim 1, wherein the remote monitor initiates an audible or visual alarm if the biometric signal exhibits a predetermined property.

16. A monitoring system, comprising:
   at least one biosensor for generating a biometric signal from a measured parameter of a person;
   a transmitter connected to the biosensor for wirelessly transmitting the biometric signal over short range using Bluetooth technology;
   a receiver not disposed in or coupled to a mobile telephone, located close to the person or receiving the transmitted biometric signal and displaying the biometric signal on a display device of the receiver;
   and transmitting the biometric signal or a signal based on the biometric signal using General Packet Radio Service (GPRS); and
   a monitor for receiving the biometric signal or a signal based on the biometric signal transmitted using General Packet Radio Service (GPRS) from the receiver.

* * * * *